(12) United States Patent
Malin

(10) Patent No.: US 7,544,329 B2
(45) Date of Patent: Jun. 9, 2009

(54) AIR-CONDITIONED STORAGE CUPBOARD

(75) Inventor: Cosmas G. Malin, Mauren (LI)

(73) Assignee: Liconic AG, Nendeln (LI)

( * ) Notice: Subject to any disclaimer, the term of this patent is extended or adjusted under 35 U.S.C. 154(b) by 790 days.

(21) Appl. No.: 10/470,384

(22) PCT Filed: Jan. 25, 2002

(86) PCT No.: PCT/IB02/00221

§ 371 (c)(1),
(2), (4) Date: Jan. 21, 2004

(87) PCT Pub. No.: WO02/059251

PCT Pub. Date: Aug. 1, 2002

(65) Prior Publication Data

US 2004/0115101 A1   Jun. 17, 2004

(30) Foreign Application Priority Data

Jan. 26, 2001 (CH) .................................. 136/01

(51) Int. Cl.
 *B01L 9/00* (2006.01)
(52) U.S. Cl. ..................................................... 422/104
(58) Field of Classification Search ......... 414/147–332; 422/63–104; 435/303.1–303.3, 809; 237/3, 237/14, 91 A; 236/2–5
See application file for complete search history.

(56) References Cited

U.S. PATENT DOCUMENTS

| 4,111,753 A | 9/1978 | Folsom et al. |
| 4,250,266 A | 2/1981 | Wade |
| 4,696,902 A | 9/1987 | Bisconte |
| 4,742,504 A | 5/1988 | Takasuka et al. |
| 4,815,055 A | 3/1989 | Fago, Jr. |
| 4,868,122 A | 9/1989 | Kominek et al. |
| 4,871,676 A | 10/1989 | Yamada |
| 4,907,889 A | 3/1990 | Simone |
| 4,912,575 A | 3/1990 | Shiosaki |
| 4,923,816 A | 5/1990 | Heeg et al. |
| 4,981,409 A | 1/1991 | Hirose et al. |
| 5,143,193 A | 9/1992 | Geraci |
| 5,449,229 A | 9/1995 | Aschenbrenner et al. |

(Continued)

FOREIGN PATENT DOCUMENTS

CH    690 962    3/2001

(Continued)

OTHER PUBLICATIONS

Astra Zeneca poster "An Advanced Approach to Cell Culture Automation using acCellerator™" published 2001.

(Continued)

*Primary Examiner*—Jill Warden
*Assistant Examiner*—Imran Akram
(74) *Attorney, Agent, or Firm*—Greenblum & Bernstein, P.L.C.

(57) ABSTRACT

The invention relates to a climate controlled cabinet with a common controller (300) for climate and handling of the goods to be stored. By means of this design the construction and operation can be simplified and the climate control can be improved. To further improve the climate control, a heating as well as a cooling device (242, 244) are provided such that heat generated by the handling device (620) can be dissipated when necessary.

6 Claims, 8 Drawing Sheets

U.S. PATENT DOCUMENTS

| | | |
|---|---|---|
| 5,470,744 A | 11/1995 | Astle |
| 5,733,024 A | 3/1998 | Slocum et al. |
| 5,735,587 A | 4/1998 | Malin et al. |
| 5,783,439 A * | 7/1998 | Reichler et al. ........... 435/286.1 |
| 5,788,448 A * | 8/1998 | Wakamori et al. ..... 414/222.02 |
| 5,961,323 A * | 10/1999 | Lee ............................. 432/241 |
| 6,059,507 A | 5/2000 | Adams |
| 6,129,428 A | 10/2000 | Hewlwig et al. |
| 6,323,035 B1 | 11/2001 | Kedar et al. |
| 6,475,776 B1 | 11/2002 | Higuchi |
| 6,478,524 B1 * | 11/2002 | Malin ......................... 414/283 |
| 6,489,524 B1 * | 12/2002 | Sabahi et al. ............... 570/181 |
| 6,568,770 B2 | 5/2003 | Gonska et al. |
| 2001/0043031 A1 | 11/2001 | Gonska et al. |
| 2002/0063077 A1 | 5/2002 | Ferger et al. |
| 2002/0163283 A1 | 11/2002 | Ferger |
| 2003/0085218 A1 | 5/2003 | Kauschke et al. |
| 2003/0085230 A1 | 5/2003 | Hessler |

FOREIGN PATENT DOCUMENTS

| | | |
|---|---|---|
| DE | 659150 | 4/1938 |
| DE | 2254218 | 5/1974 |
| DE | 19816962 | 10/1999 |
| DE | 198 57 282 A1 | 6/2000 |
| DE | 200 04 202 | 7/2000 |
| DE | 19903958 | 8/2000 |
| EP | 0154536 | 11/1985 |
| EP | 0 281 547 | 9/1988 |
| EP | 0 569 214 A2 | 11/1993 |
| EP | 0 725 133 | 8/1996 |
| EP | 1 155 743 | 5/2001 |
| EP | 1 256 808 A1 | 11/2002 |
| EP | 1 354 623 A1 | 10/2003 |
| FR | 841569 | 1/1938 |
| FR | 2 788 042 A1 | 7/2000 |
| GB | 2174714 | 11/1986 |
| GB | 2 228 989 | 9/1990 |
| JP | 11313666 | 11/1999 |
| JP | 2001000171 | 1/2001 |
| JP | 2001000172 | 1/2001 |
| WO | WO 92/14550 | 9/1992 |
| WO | WO 93/09440 | 5/1993 |
| WO | 94/01780 | 1/1994 |
| WO | WO 98/05753 A1 | 2/1998 |
| WO | WO 98/10054 | 3/1998 |
| WO | WO 99/15905 | 4/1999 |
| WO | WO 02/052511 | 7/2002 |
| WO | WO 02/059251 A2 | 8/2002 |

OTHER PUBLICATIONS

"Cytomat" product information published on the Internet on Apr. 30, 2001.

Heraeus Instruments Brochure "BB 16 $CO_2$ Incubator" imprint E 5C 8/993-4t-top.

Heraeus/Kendro sales brochure Heracell Laboratory $CO^2$ Incubators; imprint Printed in USA (Mar. 2004) S00289.

* cited by examiner

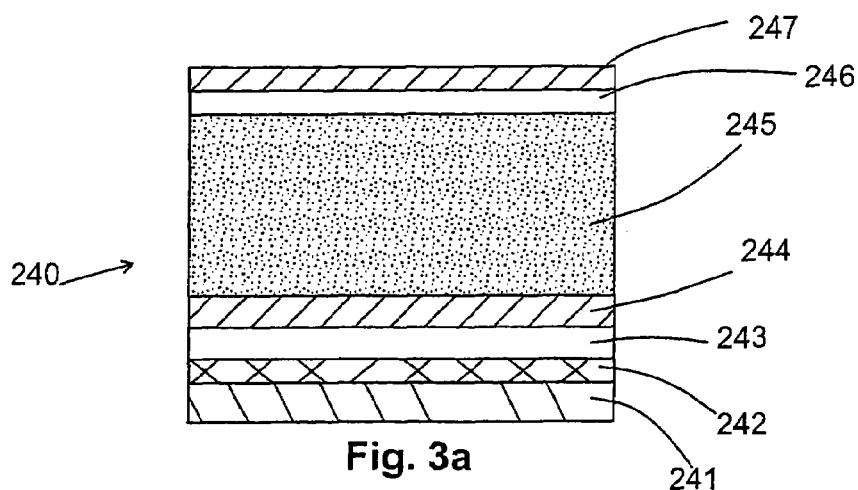
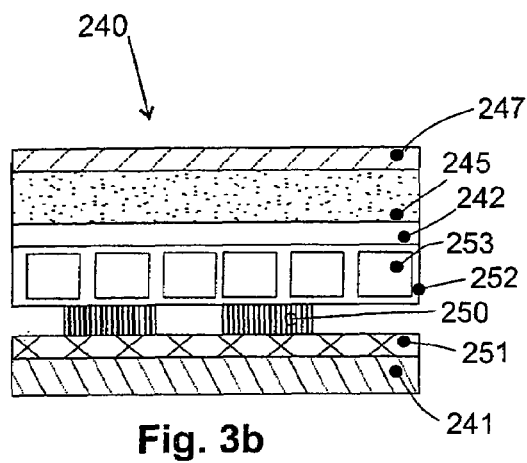 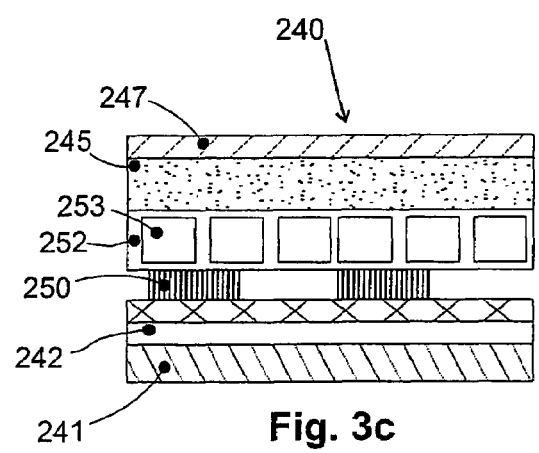
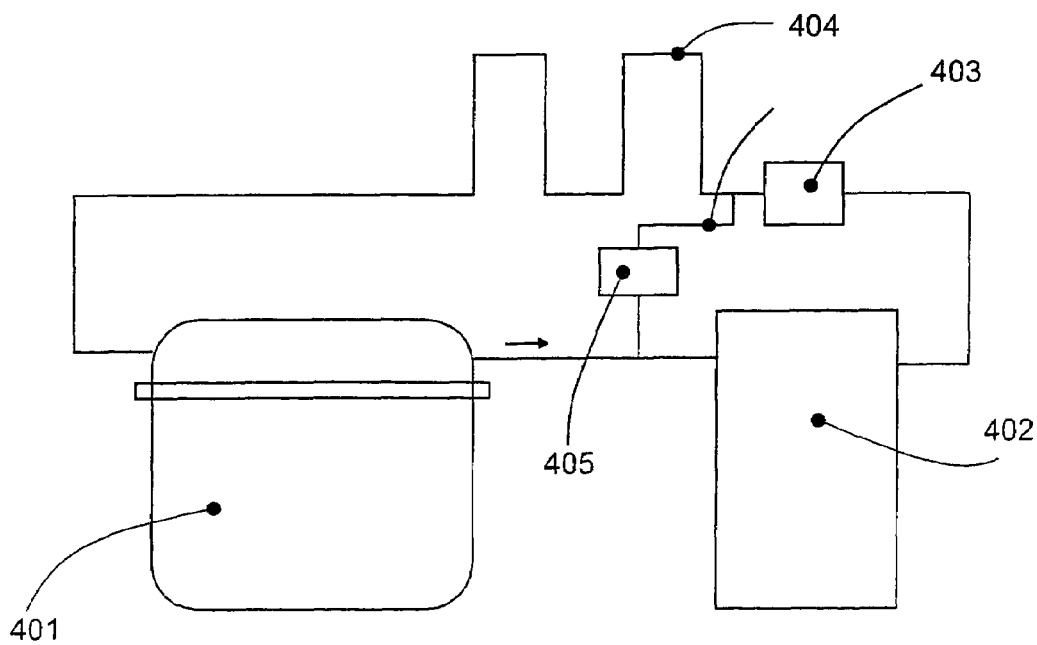

AIR-CONDITIONED STORAGE CUPBOARD

CROSS REFERENCE TO RELATED APPLICATIONS

This application claims the priority of Swiss patent application 0136/01, filed 26 Jan. 2001, the disclosure of which is incorporated herein by reference in its entirety.

BACKGROUND OF THE INVENTION

The invention relates to a climate controlled cabinet and a method for operating such a cabinet according to the preamble of the independent claims.

In substance research and microbiology the used objects must be stored under exactly predefined climatic conditions. The temperatures of the storage range typically approximately from the freezing point of water up to room temperature. The objects usually consist of containers for several liquid probes. The volumes of the probes are becoming smaller and smaller, and the logistics of the objects are increasingly carried out automatically. The capacity of the storage systems increases and, often, several such storage systems are used within one system. The value of the objects stored in the storage systems is extremely high and can be a multiple of the costs of the whole system. An accidental misidentification between objects must be prevented at any circumstance.

Today, storage systems are offered with integrated handling device for manipulating the objects. In WO98/05753 and U.S. Pat. No. 6,129,428, a climate controlled cabinet with automatic access feature is described. A user door and an automatically operable auxiliary door as well as, within the climate controlled cabinet, a positionable carousel with a handling device are provided. The integrated handling device comprises, necessarily, sensors and driving motors. Both give off heat to the climate controlled chamber. Because of the high insulating values of the cabinet insulation, even small heat sources can lead to substantial inherent warming of the climate controlled chamber and to undesired condensation at the walls, or they even make it impossible to maintain the desired temperature. In this device, the objects can be removed easily and quickly in case of a defect by using storage towers. The storage density per laboratory area in this system is, however, small. Also disadvantageous is the design of the storage towers, which does not allow a secure manual loading and unloading of the objects to be stored, does not have the mechanical precision required for automatic access and can even represent a danger of injury at the sharp edges.

Another apparatus uses shelves for receiving the objects. Such embodiments can, basically, be constructed to be as large as required, but they have the decisive disadvantage that the objects can only be loaded or unloaded manually in complicated manner and at a large risk of misidentification.

In CH 690 645 a climate controlled cabinet with user door and automatically operable auxiliary door is described, wherein fixedly arranged storage towers and a handling device are arranged within it. Such designs are only suited for a small number of storage towers and are therefore not suited for being used in larger systems.

In EP 1 155 743 a transport device with a drive arranged on a scoop and a counter weight is shown. This arrangement is not suited for a large number of accesses. If the substances have to remain within the cabinet for a long time, the transport system should, however, be maintenance free because maintenance work causes a loss of climatization. A further disadvantage of the device according to this publication is that the arrangement of the scoop drive degrades the usage of available space if the scoop mechanism is used in connection with a carousel in a climate controlled cabinet because the horizontal arrangement of the scoop drive requires a large lateral displacement for the cog rail. This, and the length of the motor of the scoop drive require the tapered front and back end of the scoop holder to become larger. For an arrangement of the scoop mechanism in the corner of a climate controlled chamber, as it is usual for carousel systems, this requires the carousel to be moved further away from the corner, which in turn requires the climate controlled chamber to be larger.

A common trait of the above devices is that, apart from the automatic access, they achieve an improvement of climatic stability by means of a small auxiliary door. When access occurs very frequent and at short time intervals, however, undesired climatic fluctuations occur also for these devices. Objects that are removed from the climate controlled chamber require, furthermore, substantial time until they reach the desired storage temperature again. This disadvantage is particularly disturbing because, in storage applications, the same object has often to be removed from the climate controlled chamber and fed back repetitively in short temporal intervals. Furthermore, the known devices cannot satisfy the desire for high access times even for large access paths while being maintenance-free at the same time.

In storage applications, a particular significance has to be attributed to humidity, for two reasons. First, it suffers much more under accesses than, for example, temperature, and, second, it determines the evaporation limited storage duration of the objects in the climate controlled chamber. Maximum humidity—typically for solutions in water—may be desired, as well as accurately defined humidity values, e.g. when using hygroscopic solutions, such as DMSO.

Adding a cooling device is, in the concerned applications, not possible without further measures because cooling is problematic when the humidity is high. For achieving high humidity, incubators of known type comprise insulation plates arranged at a given distance from the incubation chamber and thus form an air coat around the incubation chamber. This results in a homogeneous temperature distribution on the wall of the incubation chamber. If this hollow space were cooled, condensed water would result.

For an insulation suited for cooling, the cavity would have to be filled by foaming. This would, however, cause a loss of the homogenization of the temperature that was achieved by the cavity. Furthermore, foaming would require complicated scaffolding for receiving the forces generated by the foaming process. Finally, a foamed isolation can hardly be opened anymore. This would make maintenance or repair work for components arranged around the climate controlled space impossible or at least difficult. Also, building a scaffolding is expensive. For the small product life times, small numbers of units and large product diversity in the market of automatic incubators, such investments could not be amortised. Commercial standard devices do not have the desired dimensions for the climate controlled chamber. Also, the usual cooling used in such devices, where a cooling member is arranged in the climate controlled chamber or in a extended part of the climate controlled chamber, would lead to a drying out of the climate controlled chamber. This is caused by the fact that for reaching a temperature decrease, the temperature of the cooling member must be lowered substantially below the desired cooling temperature.

The usual closed loop control of the temperature in cooling devices of known type occurs by switching the chiller on and off. In order to keep the life time of the chiller at an acceptable level, switching has to take place at comparatively large time intervals. This has the disadvantage that comparatively large temperature fluctuations are observed. In addition, it is disadvantageous that vibrations occur when switching on and off, which can affect the precision of the handling device.

Due to the heat generation of the handling device, the quality of the climate that can be achieved is impaired. Climate fluctuations and recovery times are substantial, in particular during a fast series of accesses. Devices of the above type are used in complicated and costly systems, into which they have to be integrated with a great effort. Their limited usability is therefore especially noticeable as a disadvantage. Because of the lacking versatility it is therefore necessary to use, depending on the application, several devices within one system.

Just as humidity, gases are reacting very strongly to access. Even if the access occurs through a comparatively small opening, its opening is connected to a distinct drop in gas concentration. The known devices for measuring gas concentration are arranged in the climate controlled chamber and have to withstand high humidity values. This substantially reduces the usability of sensors, and sensors must be used that have disadvantageous properties, such as low effective signals and drift.

Finally, the known devices are complicated to integrate into a host system because many functions must be implemented by the integrator and a plurality of interfaces are necessary, or certain functions cannot be carried out by the host system at all or certain values are not accessible for the same.

SUMMARY OF THE INVENTION

The object of the present invention is to fight at least a part of the disadvantages mentioned above. In particular, a good control of the climate should be achieved and/or the design or construction and maintenance should be simplified while achieving a similarly good control.

In a first aspect of the invention, a climate controlled cabinet is provided that has a common controller for the climatization device and for the handling device. This allows to use synergies. In particular, a common interface can be provided. Furthermore, the climate control can be adapted to the current process steps of the handling device, e.g. when opening the climate controlled chamber for handling objects.

In another aspect of the invention, a heating device and a cooling device are provided in the climate controlled cabinet. In this manner, an improved independence of the climate temperature from the environmental temperature and heat generation of the handling device is achieved. In particular, a method for operating a climate controlled cabinet is provided where at least part of the heat generated by the handling device is actively withdrawn by means of the cooling device even if the desired temperature is higher than the environmental temperature.

In a further aspect of the invention, a temperature adaptation device is provided inside or outside of the climate controlled chamber. The handling device is designed for temporarily bringing the object to be entered into storage or removed from storage into contact with the temperature adaptation device prior to moving it to its storage position or after removing it from its storage position. This allows to quickly match the temperature of the object with the current requirements.

When entering objects into the climate controlled cabinet, the temperature adaptation device can be used for quickly matching the temperature of the object with the chamber temperature without causing fluctuations of the chamber temperature. If the temperature in the chamber is higher than the temperature of the environment, a heated temperature adaptation device is preferably provided outside the climate controlled chamber such that the object temperature can be increased before the object is introduced into the chamber. This prevents the formation of condensation. In cooling applications, a temperature adaptation device inside the climate controlled chamber, on which the object temperature can be lowered quickly, is preferably used.

In a further aspect of the invention, the climate controlled cabinet is provided with a centering device, which allows a self-centering coupling to an external system or device, such as an external object conveyor system. This simplifies the design and modification of corresponding plants.

In another aspect of the invention, several storage towers are arranged on top of each other inside the climate controlled chamber. This improves space usage in the vertical direction. It leads to an increase in storage capacity while simultaneously allowing a simple manual handling. Alternatively or in addition to this, higher storage towers reinforced by at least one stiffening member can be used.

A further aspect of the invention relates to a storage tower of metal with lateral ledges forming supports for receiving the objects. Each ledge is a metal member friction locked or positively locked to one of the side walls. This simplifies production while the ledges can still be manufactured accurately. Due to its metal design the storage tower can be autoclaved.

In another aspect the walls of the climate controlled cabinet are manufactured from metal sheets. A part of the walls has bent edges that the corresponding next walls can be attached to. This simplifies the manufacture of the climate controlled cabinet.

In a further aspect, the handling device of the climate controlled cabinet comprises a scoop holder that can be pivoted about a vertical axis, as well as be displaced parallel to the vertical axis. The scoop holder holds the scoop, which can be extended perpendicularly to the vertical axis by means of an extension drive mounted to the scoop holder. The extension drive is arranged at the rear end of the scoop holder and the longitudinal axis of the extension drive (624) is vertical. This has the advantage that the space at the rear end of the scoop holder is well used.

Another aspect of the invention relates to climate controlled cabinets in the climate controlled chamber of which at least one rotatable carousel is provided, in which a plurality of storage positions for receiving the objects to be stored is arranged in star shaped manner around an axis of the carousel. The handling device has a scoop, which can be displaced horizontally and vertically and be pivoted about a vertical axis. For compensating the weight during vertical movements of the scoop, a counter weight is provided in the carousel axis and attached via a weight deflection. This allows a good exploitation of the space in the carousel axis.

BRIEF DESCRIPTION OF THE DRAWINGS

Further embodiments, advantages and applications of the invention are given in the dependent claims and in the now following description, which makes reference to the figures. These show:

WAYS FOR CARRYING OUT THE INVENTION

Figure 1A:
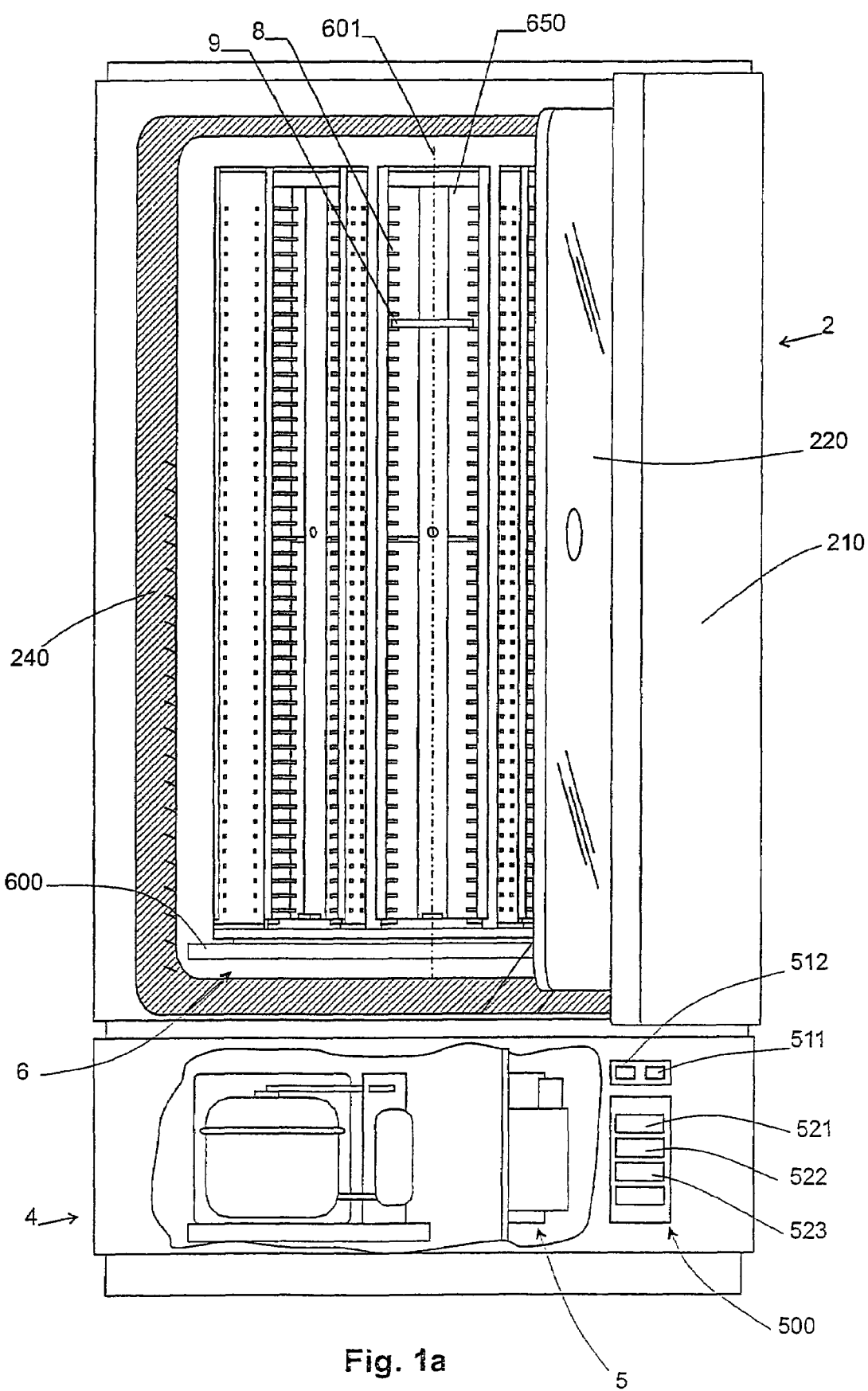
FIG. 1*a* a front view of a first embodiment of the climate controlled cabinet.

Common to all embodiments of the climate controlled cabinet shown here the climate controlled cabinet comprises a climate controlled chamber 2 and a control chamber 4.

A plurality of storage-positions 8 for the objects 9 to be stored are provided in climate controlled chamber 2. It has an outer and an inner user door 210 and 220, respectively, at the front side and an auxiliary door 15 at the back side. The user doors 210, 220 serve for manual access to the interior of climate controlled chamber 2. Outer user door 210 is thermally insulated and non-transparent, the inner user door has a transparent, thermally insulated double glazing. Within climate controlled chamber 2, a handling device 620 is arranged for automatically transporting the objects between the storage positions and a transfer position outside the climate controlled cabinet, for which purpose auxiliary door 15 is used.

A controller as well as various apparatus 5 for generating heat, cold and/or controlled atmosphere are arranged in control chamber 4. An interface is provided for the computer controlled operation of the climate controlled cabinet.

The interior of climate controlled chamber 2 is kept at fixed temperature and under given atmospheric conditions by means of a climatization device. For this purpose, the climatization device comprises the mentioned apparatus for generating heat, warmth and/or controlled atmosphere, as well as various parts described in the following.

In FIG. 1a an embodiment of the climate controlled cabinet is shown. It comprises a display 500 with display fields 512-523 for displaying important information, such as the temperature, relevant humidity and $CO_2$ content in climate controlled chamber 2. An acoustic alert system 512 informs the user about inadmissible states of the system. In addition, one or more input elements 511 are provided, by means of which a part of the functions of the climate controlled cabinet can be controlled.

In the embodiment of FIG. 1a, a carousel 600 rotatable about a vertical axis 601 is arranged in climate controlled chamber 2. Reinforced storage towers 650 are removably stored on carousel 600.

Figure 1B:
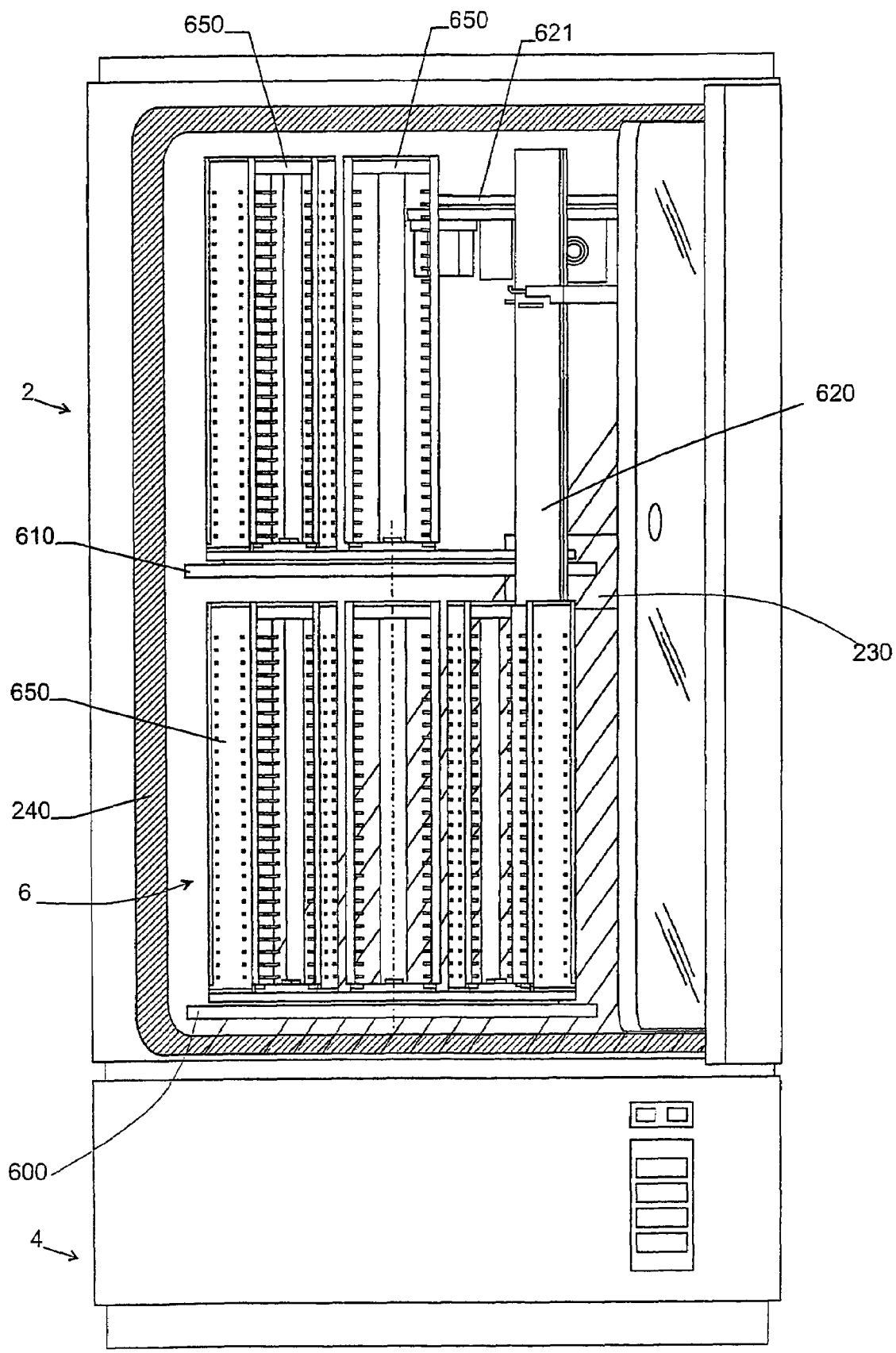
FIG. 1*b* the front view of a second embodiment of the climate controlled cabinet, FIG. 2*a* the front view of an embodiment of a storage tower, FIG. 2*b* a side view of the storage tower of FIG. 2*a*, FIG. 2c a detail of the storage tower of FIG. 2a, FIG. 2d an embodiment of a stiffening device of the storage tower, FIG. 3a a sectional view of an insulation according to the invention, FIG. 3b a sectional view of a first temperature control device with Peltier elements, FIG. 3c a sectional view of a second temperature control device with Peltier elements, FIG. 3d a block circuit diagram for the cooling control according to the invention with compressor aggregate, FIG. 4a the side view of an embodiment of a temperature adaptation device, FIG. 4b the side view of an embodiment of the climate controlled cabinet with two temperature adaptation devices, FIG. 5a the side view of a climate controlled cabinet with centering device, FIG. 5b the top view of the climate controlled cabinet with centering device, FIG. 6a the top view of a climate controlled cabinet with an advantageous scoop drive, FIG. 6b a top view of a handling device with counter weight, and FIG. 7 a block diagram of the controller of the device according to the invention.

In FIG. 1b, a climate controlled cabinet with a climate controlled chamber 2 is shown in which several storage towers 650 and two rotatable carousels 600, 610, respectively, are arranged on top of each other for enlarging the storage capacity for a given footprint area. By arranging two carousels on top of each other, a stiffening of the control towers 650 on the carousels 600, 610 can be dispensed with.

The carousels of the climate controlled cabinets of FIGS. 1a and 1b are loaded and unloaded by means of a handling device 620 (only visible in FIG. 1b). Handling device 620 comprises a scoop 621 for receiving an object, wherein scoop 621 can be rotated about a vertical axis of rotation and be displaced parallel to the axis of rotation and be extended perpendicularly to the axis of rotation. Such a handling device is described in U.S. Pat. No. 6,129,428.

Figure 2A:
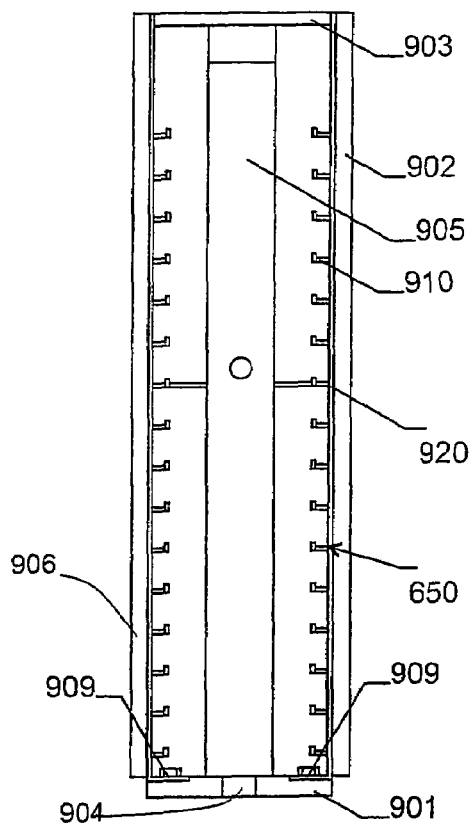
Figure 2B:
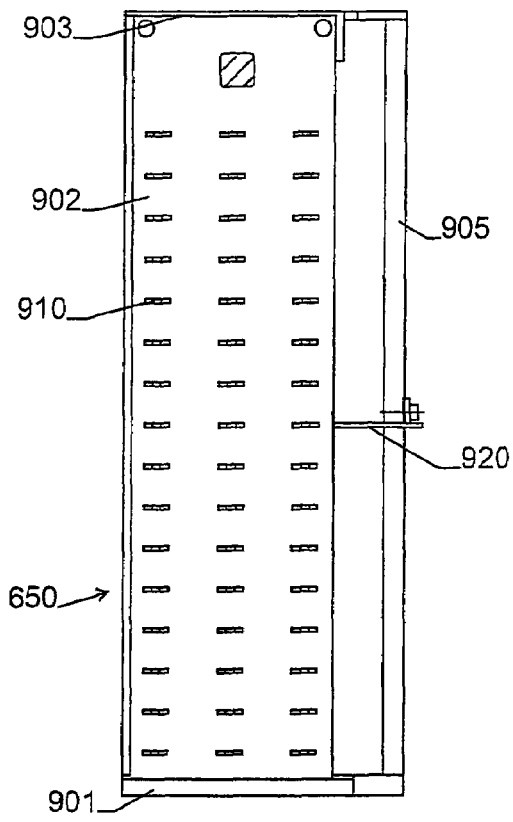

FIGS. 2a and 2b show an embodiment of a storage tower 650. A left and a right side wall 902, 906 of sheet metal are arranged on a base plate 901 by means of a holding device 904. The side walls 902, 906 are connected at their upper ends via a holder plate 903. At the back side of the storage tower, a wall member 905 is arranged as connecting member between holder plate 903 and base plate 901. Lateral ledges 910 for receiving the objects are arranged on the walls 902, 906. The ledges 910 are metal parts, which are mounted to one of the side walls in positively locked or friction locked manner. Hence, they can be manufactured separately and with high precision. Since they consist of metal, they can still withstand high temperatures (e.g. during autoclavation).

The ledges 910 are preferably made from metal sheets and comprise front and rear ends bent upwards, which form retention pins 912 and prevent the objects from sliding off.

Figure 2C:
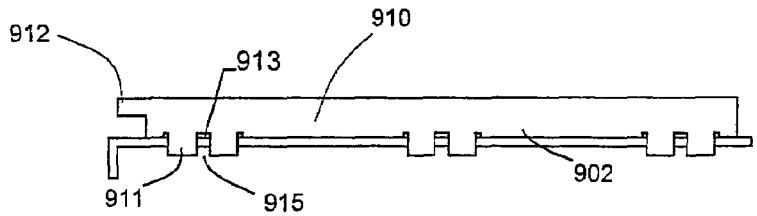

FIG. 2c shows a detailed view of a ledge 910. At a side facing the side wall 902 or 906, respectively, of the storage tower, ledge 910 comprises splay members 911. The splay members 911 are led through openings 913 of the side walls 902, 906. Each splay member 911 consists of two tongues. A gap 915 is arranged between the tongues, by means of which the tongues 911 can be splayed by means of a tool and are thus held in positively locking or at least friction locking manner in the openings 913 of the side walls 902, 906.

To improve stability, the side walls 902, 906 rest with bent ends 909 on base plate 901 and are screwed to base plate 909 or attached to the base plate via the ends 909 in different manner.

Since storage tower 650 is a removable transport container, the proper weight of which should be small, it is manufactured from a comparatively thin metal sheet. Due to the small material thickness, the storage towers built in this manner can only be manufactured for a limited height with required precision. For this reason, at least one stiffening member 920 can be arranged between the upper and the lower end of the storage tower.

Figure 2D:
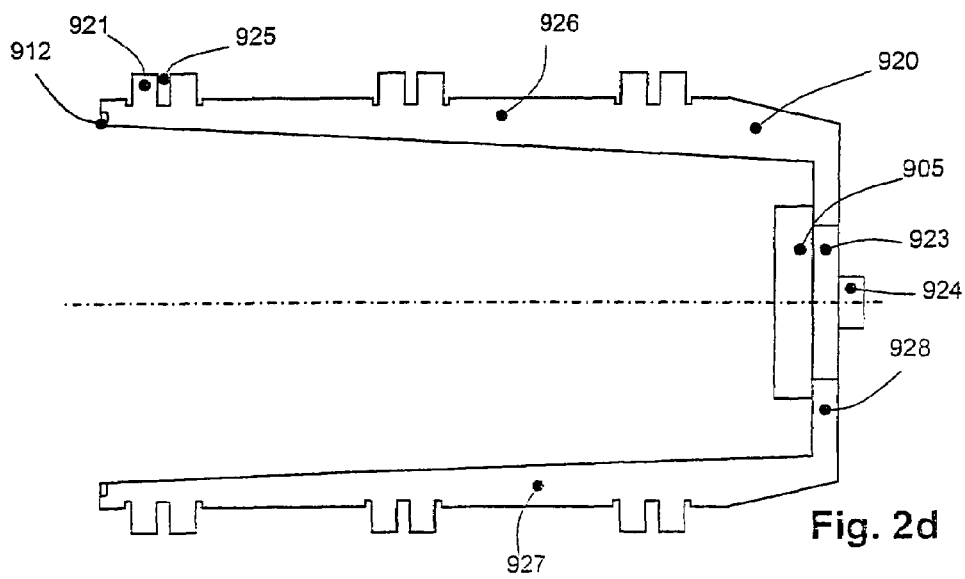

FIG. 2d shows an embodiment of stiffening member 920. It provides an exact positioning of the side walls 902, 906. Analogously to the ledges 910, stiffening member 920 has ledge surfaces 926, 927, which are connected via a connecting web 928 extending behind wall member 905. Connecting web 928 is connected to wall member 905. For lateral attachment, stiffening member 920 comprises, analogously to the ledges 910, lateral tongues 921 with gaps 925, which are introduced into corresponding openings of the side walls 902, 906 and splayed therein.

At the rear side, an attachment plate 923 connected to wall member 905 by means of a screw 924 is arranged on stiffening member 920.

Due to the exclusive application of steel and the shown arrangement of the parts, a particularly high long time stability and shock resistance of the storage tower is achieved. Furthermore, the storage towers withstand high temperatures, as they occur during autoclavation.

FIG. 3a shows the design of a temperature control device 240, which is part of the climatization device mentioned before. Temperature control device 240 is, with the exception of the door areas, arranged around the whole climate controlled chamber 2. A heating surface 242 and a cooling surface 244 are arranged around inner wall 241 of the climate controlled chamber. The two surfaces are, when viewed from the inside of climate controlled chamber 2, designed as two metal layers located on top of each other. Heating surface 242 is designed as a metal sheet or foil with glued-on or integrated heating wires. Cooling surface 244 is also a metal sheet or metal foil with integrated or attached tubes for the cooling liquid. Because the heating wires and the tubes, respectively, are connected to each other by means of the metal sheet or the foil, the temperature distribution is made homogeneous, which reduces undesired formation of condensate on the chamber walls.

To improve the homogeneity of the temperature distribution further, an air gap 243 is provided. Because in particular the tubes of the cooling surface cannot be arbitrarily small nor be arranged at a high density, it is advantageous to arrange air gap 243 in the area between cooling surface 244 and inner wall 241. In FIG. 3a, air gap 243 is located between cooling surface 244 and heating surface 242, but it can also be located between heating surface 242 and inner wall 241.

Heating surface 242 and cooling surface 244 are surfaces that correspond at least to the surface of the climate controlled chamber wall and that surround climate controlled chamber 2 on all sides (with the exception of the door areas). The planar arrangement of the heating and cooling surface allows to form an optimally large area for coupling in the temperature. In addition, a homogeneous temperature distribution on the wall of the climate controlled chamber is achieved. It is particularly advantageous that the cooling device is arranged over all walls of climate controlled chamber 2 (with the possible exception of the areas of the user doors 210, 220 and auxiliary door 15) and cools the same homogeneously. This reduces condensation, and a high humidity can be achieved.

Heating surface 242, cooling surface 244 and air gap 243 are surrounded by an insulation layer 245. The insulation layer is gas tight such that no air can penetrate from the outside to cooling surface 244. By surrounding cooling surface 244 on the outside by a gas tight insulation layer, an undesired condensation can be prevented.

Insulation layer 245 consists of gas tight insulation mats, which are glued to cooling surface 244 and sealed at their seams between each other. Using mats allows a gas tight construction without the need for foaming. Furthermore, the mats can be removed if required, e.g. for carrying out maintenance work on cooling surface 244.

In addition to this, a heat reflecting layer 246 can be arranged between the outer wall 247 of the climate controlled cabinet and insulation layer 245.

Hence, a heating device (e.g. in the form of heating surface 242) as well as a cooling device (e.g. in the form of cooling surface 244) are provided in the climate controlled cabinet. This is preferably also the case when the interior of climate controlled cabinet 2 is to be warmer than the environment. The cooling device allows to dissipate the heat from the driving motors of handling device 620, arranged in the interior of climate controlled chamber 2, at any time and thus to keep the temperature constant. Hence, using the cooling device makes even sense if the climate controlled cabinet is only to be used for storing objects at a temperature that, compared to the environment, is elevated, such as at 37° C. The climate controlled cabinets shown here can, however, also be used, without modification in design, for storing objects at a temperature that is reduced as compared to the environment, i.e. with any climate controlled cabinet a large range of temperatures of e.g. −20° C. (or lower) up to 70° C. (or higher) can be covered.

The embodiment of a temperature control device 240 shown in FIG. 3b uses Peltier elements for cooling and heating, respectively. The Peltier elements 50 are mounted on a thermally conducting metal sheet 251, which surrounds the inner wall 241 of climate controlled chamber 2. The thermally conducting metal sheet again serves to homogenize the cooling of the Peltier elements, which is, when compared to the complete cooling surface, point-wise only. On the second side of the Peltier elements a heat matching layer 252 is arranged. When cooling thermally conducting metal sheet 251, excess heat is dissipated to the environment via thermal matching layer 252. For improving the heat removal, heat matching layer 252 comprises cavities 253, through which a fluid for taking off heat is flowing. This fluid can be air or a liquid. Heat matching layer 252 is provided with a heating layer 251. This heating layer is active while heating the Peltier elements of the thermally conductive layer and prevents a cooling of heat matching layer 252 and a corresponding condensation on the heat matching layer. Insulation layer 245 encloses the temperature control device in gas tight manner.

In the sectional view of a temperature control device 240 view shown in FIG. 3c a heating layer 242 is arranged between wall 241 and Peltier element 250. In this arrangement, Peltier element 250 in only active when the climate controlled chamber is to be cooled. Heating of the climate controlled chamber occurs in this case directly by means of heating layer 242.

FIG. 3d shows a preferred embodiment of a chiller for cooling the cooling surface 244. It comprises—in per-se known manner—a compressor 401, which feeds a cooling fluid to a condenser 402, from where the cooling fluid reaches an injection valve 403 and from there to the actual cooling tubes 404, which withdraw heat from cooling surface 244. In addition, an auxiliary valve is arranged between the output of compressor 401 and the output of injection valve 403, by means of which condenser 402 (and injection valve 403) can be shunted. When auxiliary valve 405 is opened, the temperature of the cooling fluid in the cooling tubes 404 is increased.

The temperature of the cooling tubes and the cooling surface 244, respectively, is preferably controlled by opening and closing auxiliary valve 405 while keeping compressor 401 in operation continuously. When compared to devices where the compressor is switched on and off for temperature control, in this solution vibrations due to switching the compressor on and off are reduced and the life time of the plant is increased.

Figure 4A:
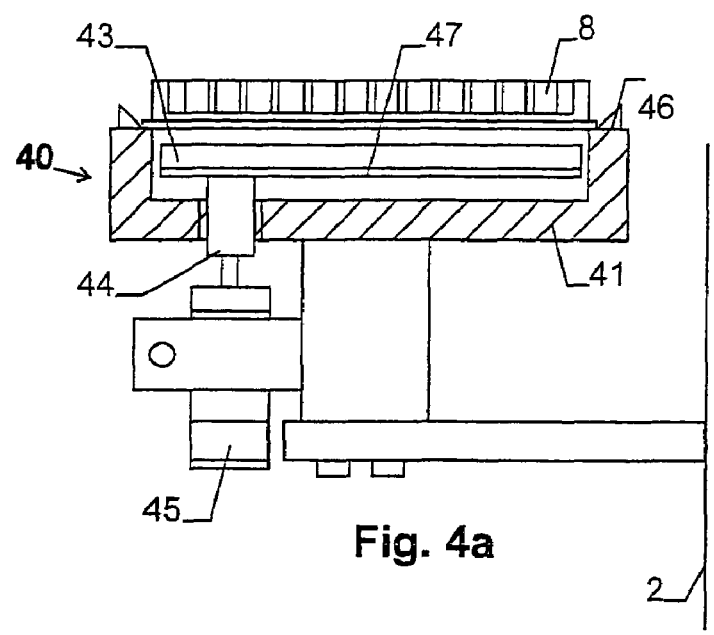

FIG. 4a shows a lateral view of a temperature adaptation device 40, as it can e.g. be arranged on the climate controlled cabinet in front of auxiliary door 15. An object 8 to be stored is arranged on a centering frame 41 with centering pins 46. Centering frame 41 has a tub shape. Inside the centering frame, there is a plate 43 that can be displaced in height. The same is fed by a temperature source 47 and can be offset vertically by means of a plate elevator 44 with a drive 45. The size of plate 43 corresponds approximately to the size of an object 8 to be stored. By lifting plate 43, a contact between plate 43 and the floor of object 8 is established. By means of this contact, the speed of the temperature settling time can be increased drastically. By an over-or underheating, respectively, of the temperature controllable plate, nearly arbitrarily short settling times can be achieved.

If an object 8 is to be brought into the climate controlled cabinet, it can first be brought onto temperature adaptation device 40. There, its temperature is matched to or at least brought close to the interior temperature of the climate controlled cabinet. Then auxiliary door 15 is opened and handling device 620 brings object 8 to the desired position inside the climate controlled cabinet.

By means of the temperature adaptation device 40 outside the climate controlled cabinet, temperature fluctuations within the cabinet caused by the heat capacity of objects brought in can be reduced.

In heating applications the temperature adaptation device 40 outside the climate controlled cabinet has the further advantage that objects are not substantially colder than its interior when they are brought inside such that a condensation is prevented.

Temperature adaptation device 40 further serves as a transfer position between handling device 620 and an external transport system.

Figure 4B:
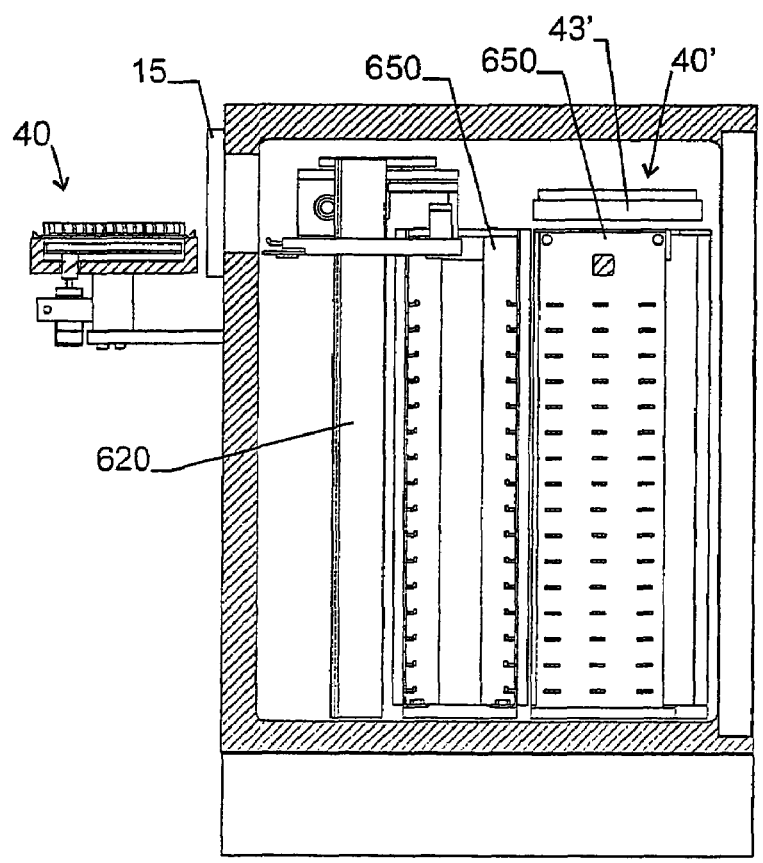

A further embodiment of a cabinet is shown in FIG. 4b, where the storage towers 650 are not arranged on a carousel but are stationary inside climate controlled chamber 2.

In the cabinet of FIG. 4b a second temperature adaptation device 40' is arranged inside the climate controlled cabinet. It comprises a metal support plate 43', which either passively matches the temperature of the cabinet or is actively heated or cooled. Preferably, it has approximately the same temperature as the interior of climate controlled chamber 2.

Temperature adaptation device 40' arranged in the interior is preferably used in cooling applications. An object to be brought into the climate controlled cabinet is first placed by handling 620 on temperature adaptation device 40', where, thanks to the heat capacity of support plate 43', its temperature falls comparatively quickly and substantially without affecting the temperature stability of the chamber to the desired value-without any condensation taking place. During this, support plate 43' serves as a heat reservoir for buffering the heat of the object.

Figure 5A:
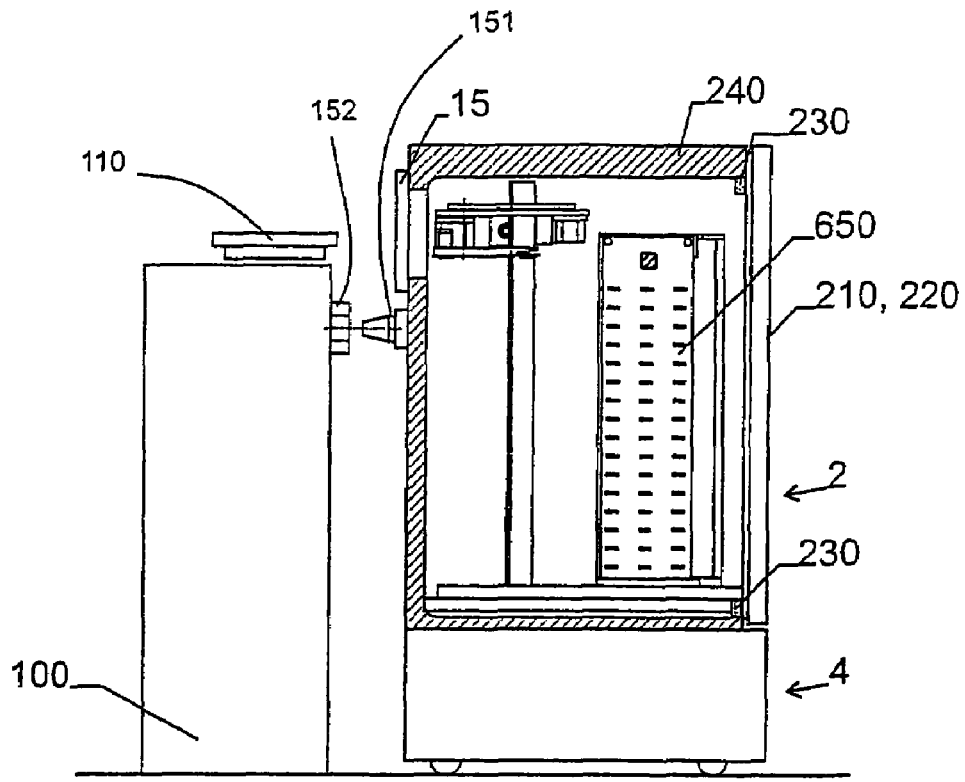
Figure 5B:
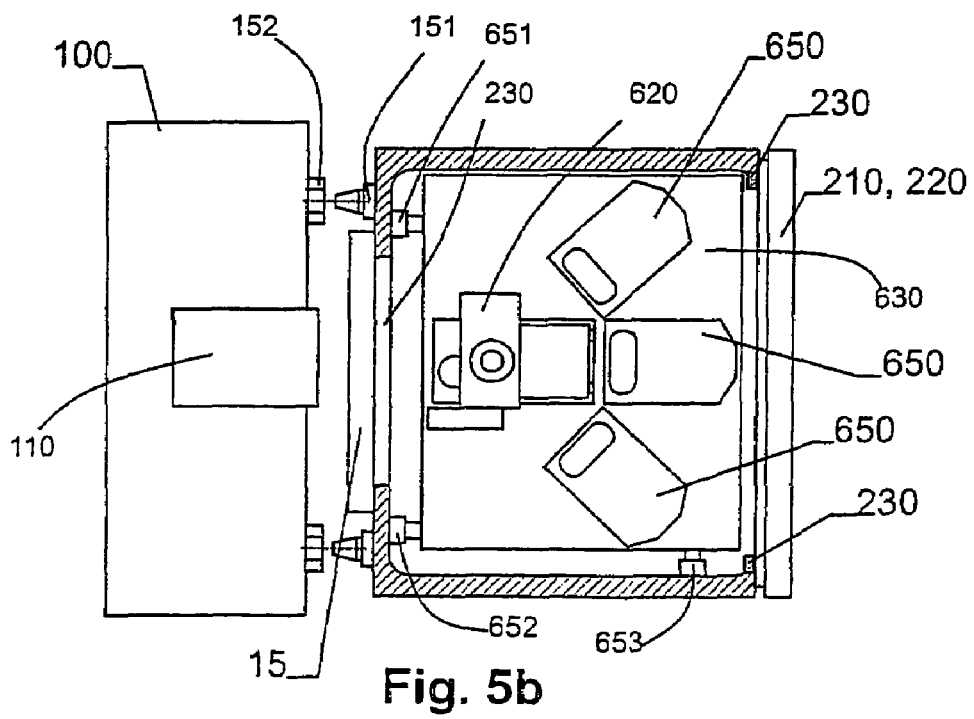

FIGS. 5a and 5b show a further embodiment of a climate controlled cabinet with three stationary storage towers 650, which are aligned to the rotational axis of handling device 620 in symmetric arrangement, wherein the handling device 620 is located between the storage towers 650 and the auxiliary door.

At least one cone 151 of a centering device is provided at the back side of the climate controlled cabinet. A matching part 152 for the centering device is mounted to an external object conveyor system 100. By means of the centering device, the climate controlled cabinet can be aligned easily and exactly in self centering manner to the external system.

As it can be seen from FIG. 5b, handling device 620 and the storage towers 650 are mounted to a base plate 630 arranged in climate controlled chamber 2. Base plate 630 is displaceably mounted in climate controlled chamber 2. The handling device 620 with the storage towers 650 can be positioned by means of adjustable horizontal stops 651, 652 and 653 by pushing two edges of base plate 630 against the stops 651, 652 and 653. The stops 651, 652 and 653 are aligned in such a manner in respect to the centering device that the storage positions, the handling device 620 and the transfer position 110 are in correct relation to each other. This allows a quick and secure positioning of the components within climate controlled chamber 2 in respect to the cones 151 and the external system 100.

The external object conveyor system 100 can e.g. comprise a transfer position 110 (e.g. of the type of temperature adaptation device 40), as well as an automatic transport system for the objects.

As can be seen from FIG. 5a, a sealing 230 is provided between the climate controlled chamber and the user doors 210, 220. Preferably, sealing 230 is heated, e.g. by means of a heating wire arranged inside the profile of the sealing, such that there is no condensation in the interior at the sealing, even at elevated temperature and humid atmosphere. This allows to increase the maximum humidity in the interior.

A heated sealing 230 can also be used for auxiliary door 15.

In order to avoid a condensation in particular for heating applications at the interior of the inner user doors 220, the inner user door can be heated. This can e.g. be achieved by heating wires on the outside of the inner user door 220 or between the inner and the outer user door or in the outer user door.

Figure 6A:
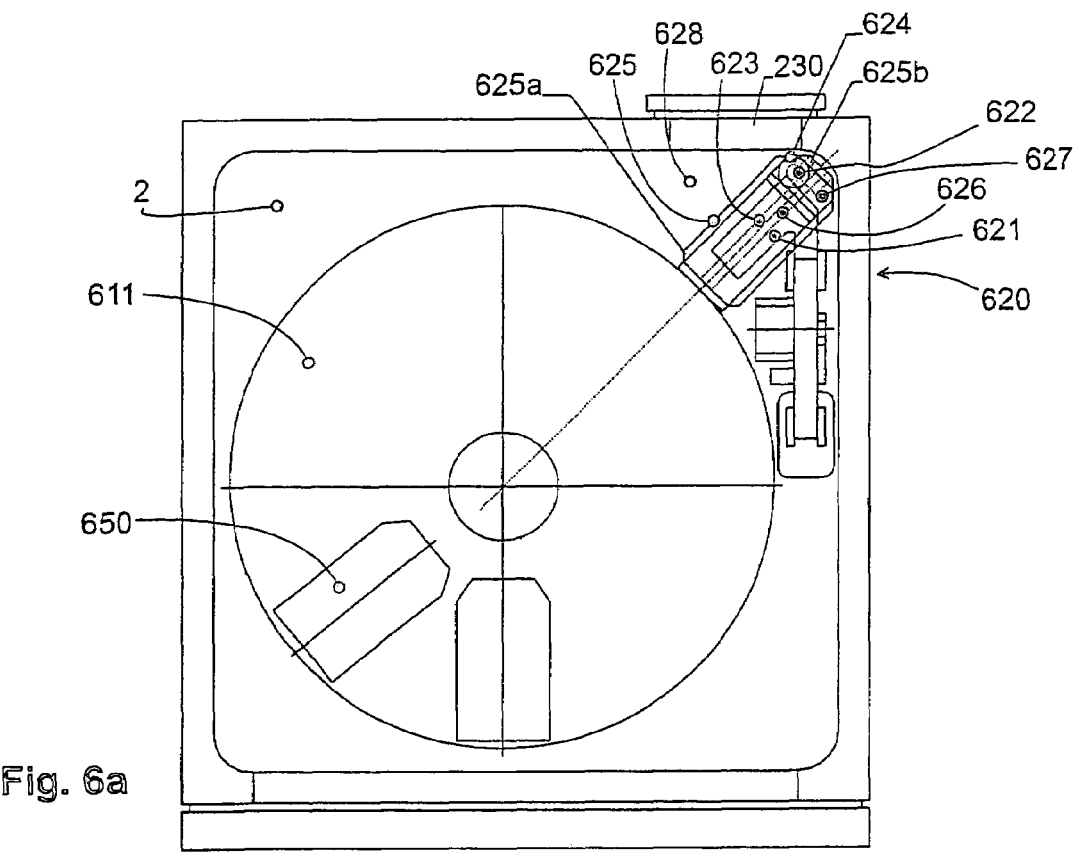

FIG. 6a shows a climate controlled cabinet with carousel 611. As shown, handling device 620 comprises a scoop holder 625 arranged in a corner of climate controlled chamber 2 and being vertically displaceable and rotatable about a vertical axis. Scoop holder 625 carries the scoop 621. It comprises a forward end 625a, beyond which scoop 621 can be extended, and a rear end 625b.

Scoop 621 is driven horizontally by means of a pinion 622 running on a cog rail 623. The extension drive 624 for extending the scoop is vertically displaceable together with the scoop. It is mounted at rear end 625b of scoop holder 625 and has a longitudinal axis perpendicular to scoop 621. Cog rail 623 is arranged at a small distance from linear guide 626 of scoop 621. In this manner, the scoop drive motor 624 is compactly arranged on the carriage part 627 of the scoop holder, which carriage part is tapered towards the rear end. The effective length of the scoop holder 625 is of particular significance for a climate controlled cabinet with carousel because, in that case, the elevator assembly of the handling device 620 is arranged in the approximately triangular space 628 formed by two side walls of climate controlled chamber 2 and the circumference of carousel 611. The part of the diagonal, however, that lies in this approximately triangular space 628 corresponds, in conventional storage systems, only to the length of the objects.

Figure 6B:
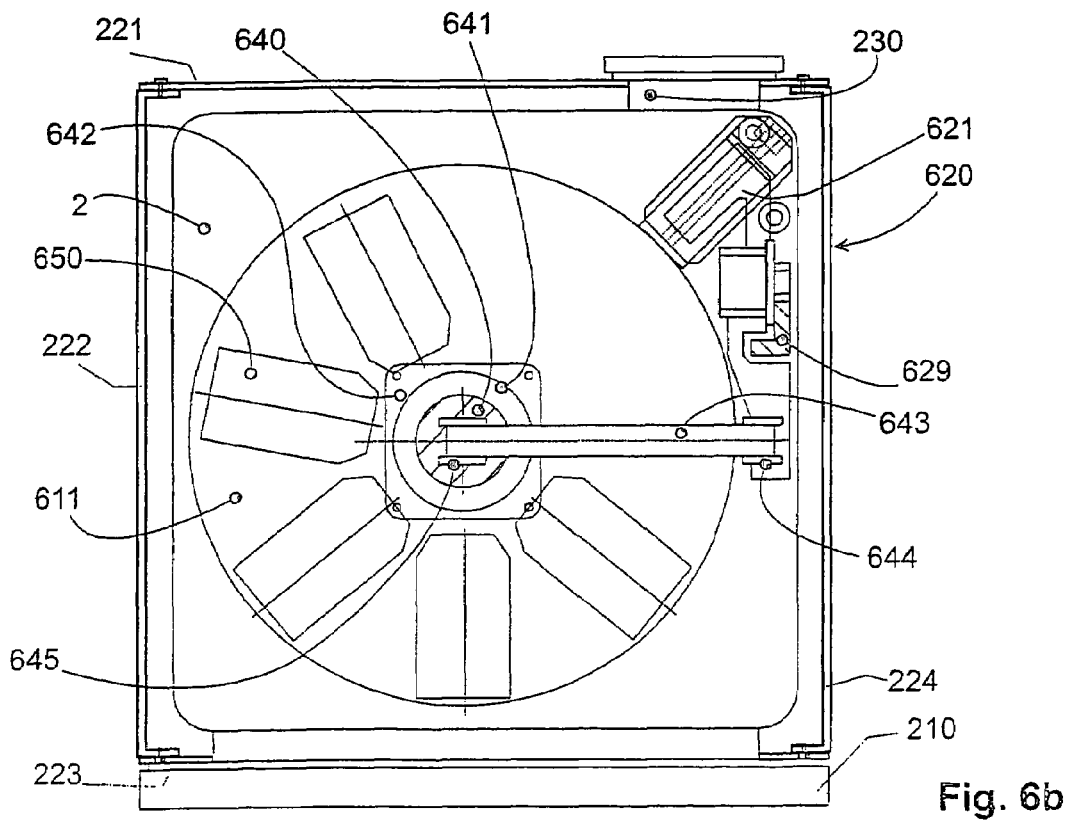

FIG. 6b shows a storage system suited for frequent access and for a quick crossing of the comparatively large paths by handling device 620 along its vertical guiding rail 629. In this embodiment, the proper weight of the vertically movable part of handling device 620 is compensated by a counter weight 640. In order to exploit the space optimally, counter weight 640 is arranged in the center of rotation of carousel 611, i.e. in the axis of the carousel. A protecting tubular shell 641 surrounds counter weight 640, which is simultaneously used as a ventilation tube. For this purpose, a blower 642 is arranged at the end section of tubular shell 541. The counter weight is hung by a flat belt 643 serving as weight deflection, which is connected to the vertically movable part of the handling device via two deflection rollers 644, 645. By using flat belt 653, the fatigue due to the substantial strain caused by the small radii of the deflection rollers 644, 645 is reduced. A flat belt 643 has a width that is large as compared to its thickness.

FIG. 6b further shows the advantageous arrangement of the housing parts meeting the requirements in view of flexibility and simplicity. A front metal sheet 223 is directly connected to the climate controlled chamber by means of insulation parts. Lateral walls 223, 224 are mounted to front metal sheet 223. A back wall is in its turn mounted to the lateral walls 222, 224. The lateral walls 222, 224 are metal sheets that are bent perpendicularly at their edges. Screw threads are provided in the bent faces. The front metal sheet and the back wall are attached to the screw threads by means of screws. Hence, only simple, in part bent metal sheets are required for the housing.

Figure 7:
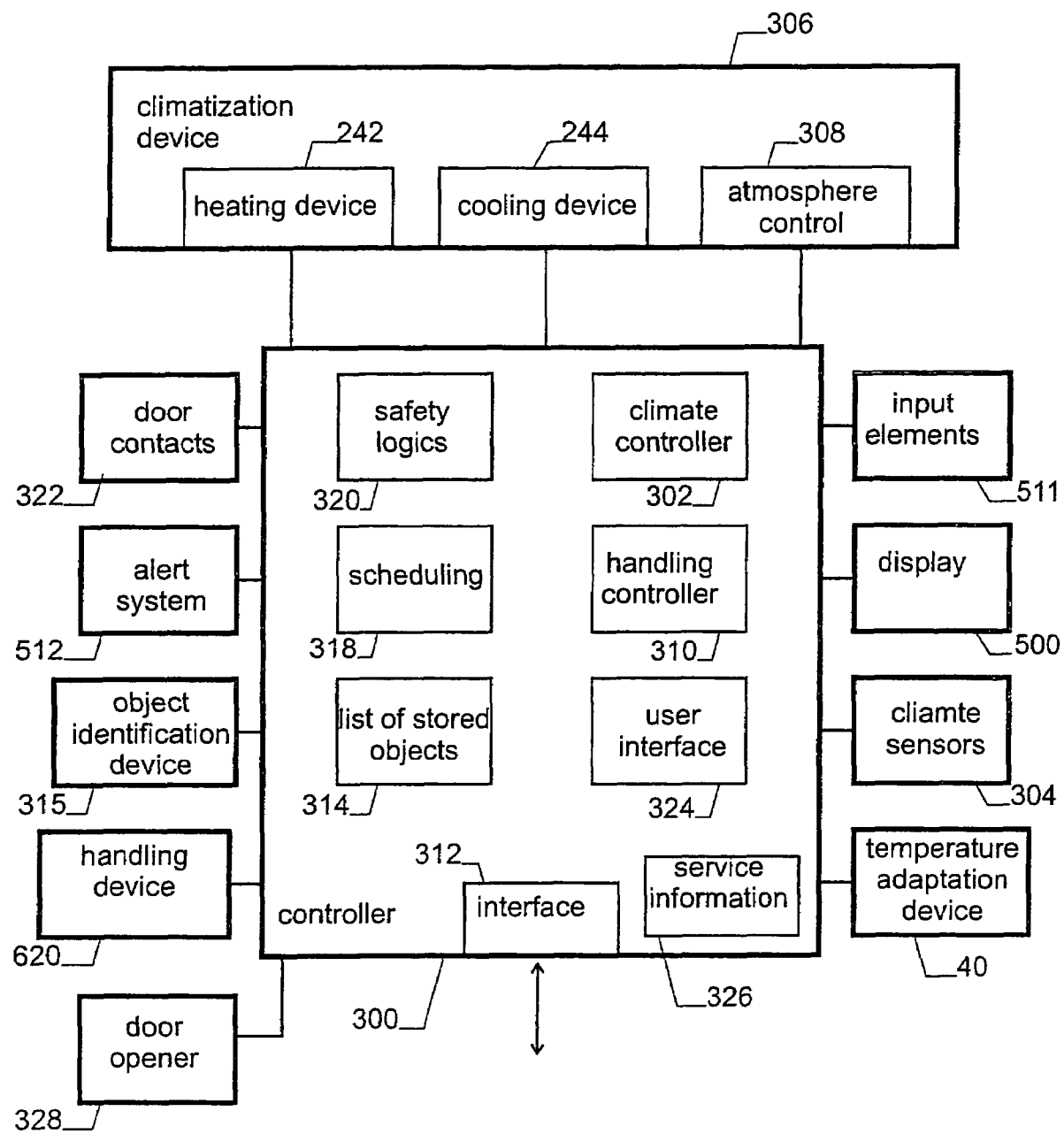

FIG. 7 shows important functional blocks of the climate controlled cabinet and in particular of controller 300 of the same. Controller 300 is based on a computer and has several functional parts, the most important of which are shown in FIG. 7.

A climate controller 302 communicates with climate sensors 304, which measure the temperature and atmosphere (e.g. humidity and $CO_2$-concentration) in climate controlled chamber 2. It controls the climatization device 306, which comprises the mentioned heating and cooling device as well as an atmosphere control, according to the sensor signals and the given desired values. Atmosphere control 308 is designed to feed a gas (e.g. $CO_2$ or $O_2$) and/or water or vapor to climate controlled chamber 2.

The climatization device 306 can also control further or other parameters of the climate controlled chamber, such as an illumination of the stored goods with light of a given spectral range.

A handling controller 310 controls the movements of handling device 620, a door opener 328 of auxiliary door 15 and the functions of temperature adaptation device 40. For this purpose, it can e.g. follow commands that are delivered through an interface 312 from a host system. But it can also, at least partially, work autonomously and e.g. determine by itself it at which free position an object to be stored is to be deposited.

A list of stored objects 314 can be provided to record which objects are deposited at which storage positions. For this purpose, it is also possible to provide an object identification device 315 at the climate controlled cabinet, which is able to identify objects, e.g. at the transfer position 110. The object identification can e.g. be designed as barcode reader or reader for electronic tags, wherein the objects are provided with a corresponding marking.

A scheduling function 318 monitors the duration of storage of each object in the storage cabinet and compares the same with given limiting values. If an object has e.g. been in the storage cabinet for a certain time, it can emit an alert, e.g. via alert system 512 or interface 312.

Safety logics 320 are provided for monitoring limiting values and, if necessary, for releasing an alert, and/or for detecting an opening of user door 210 and taking appropriate measures (alert, notification of the climatization controller). For this purpose, door contacts 322 are provided.

A function block titled "user interface" 324 assumes the control and monitoring of display 500 and input elements 511.

Interface 312 provides a common interface for substantially all functions of controller 300. In particular, the desired values of the climate controller loop 302 can be set, the operation of handling controller 310 can be controlled and the current state values of the climate controlled cabinet can be sampled via interface 312.

Finally, service information 326 is stored in controller 300, such as the accumulated time of operation, which can be read out by the user or via interface 312.

By controlling all functions of the climate controlled cabinet by means of a common controller, advantageous synergies can be achieved.

For example, controller 300 knows when auxiliary door 15 is opened and how long it will probably be opened. It can use this information for optimizing climate controller 302. Because, when opening the auxiliary door, an undesired heat exchange between the environment and the interior of climate controlled chamber 2 takes place, a temporary heating or cooling-surge can be generated upon opening (i.e. even prior to opening, during the duration of the open state, and/or after opening). Also, a loss of humidity and/or gas through the opened door can be corrected instantaneously. It is not necessary to wait for corresponding signals of the sensors 304. Controller 300 is therefore designed such that it controls the climatization device 306 in such a manner that a heat- and/or gas exchange through the opened auxiliary door 15 is counteracted upon opening auxiliary door 15 and without waiting for a change of the signals of the climate sensors 304

The controller further comprises a stand-by mode, in which the active components of the transport system are operated with reduced power when the transport system is not moving. This reduces disturbances of the sensitive climate inside the climate controlled chamber.

While the present application describes preferred embodiments of the invention, it is to be pointed out clearly that the invention is not limited thereto and can also be carried out in different manner within the scope of the following claims.

The invention claimed is:

1. A climate controlled cabinet comprising:
   a cabinet housing;
   a climate controlled chamber located within the cabinet housing;
   a climatization device for generating a given temperature and atmosphere within the climate controlled chamber;
   a plurality of storage towers arranged within the generated given temperature and atmosphere within the climate controlled chamber, wherein each storage tower comprises a plurality of storage positions arranged above each other for objects to be stored and is removable from the climate controlled chamber; and
   a handling device arranged in the climate controlled chamber for manipulating the objects,
   wherein, within the generated given temperature and atmosphere within said climate controlled chamber, at least two of the plurality of storage towers are arranged one above the other and at least two of the plurality of towers are arranged beside each other.

2. A climate controlled cabinet comprising:
   a cabinet housing;
   a climate controlled chamber located within the cabinet housing;
   a climatization device for generating a given temperature and atmosphere within the climate controlled chamber;
   a plurality of storage towers arranged within the generated given temperature and atmosphere within the climate controlled chamber, wherein each storage tower comprises a plurality of storage positions arranged above each other for objects to be stored and is removable from the climate controlled chamber;
   a handling device arranged in the climate controlled chamber for manipulating the objects; and
   at least two rotatable carousels located within the generated given temperature and atmosphere within the climate controlled chamber and arranged on top of each other for receiving the storage towers.
   wherein, within the generated given temperature and atmosphere within said climate controlled chamber, at least two of the plurality of storage towers are one arranged above the other.

3. The climate controlled cabinet of claim 1 having exactly two levels of storage towers arranged above each other.

4. A climate controlled cabinet comprising:
   a cabinet housing;

a climate controlled chamber located within the cabinet housing;

a climatization device comprising a cooling device for at least one of generating and maintaining a given temperature within the climate controlled chamber and an atmosphere control to generate a given atmosphere within the climate controlled chamber;

at least two rotatable carousels located within the climate controlled chamber and on top of each other, wherein each carousel carries a plurality of storage towers, and each storage tower comprises a plurality of storage positions arranged one above the other for objects to be stored and is removable from the climate controlled chamber;

a handling device arranged in the climate controlled chamber for manipulating the objects; and wherein, within said climate controlled chamber, at least two of the plurality of storage towers are arranged one above the other.

5. The climate controlled cabinet of claim 4, wherein the climatization device further comprises a heating device.

6. The climate controlled cabinet of claim 4, wherein the at least two rotatable carousels are arranged within the at least one of the generated and maintained temperature and the generated atmosphere within the climate controlled chamber.

* * * * *